United States Patent [19]

Wardell

[11] Patent Number: 4,532,469
[45] Date of Patent: Jul. 30, 1985

[54] APPARATUS FOR CAPACITANCE OR DAMPNESS MEASUREMENTS

[75] Inventor: Gerald E. Wardell, Killaloe, Ireland

[73] Assignee: Rynhart Research Limited, Delgany, Ireland

[21] Appl. No.: 414,676

[22] Filed: Sep. 3, 1982

[30] Foreign Application Priority Data

Sep. 10, 1981 [IE] Ireland ................................ 2109/81

[51] Int. Cl.$^3$ ............................................. G01R 27/26
[52] U.S. Cl. .................................................. 324/61 R
[58] Field of Search ............................ 324/61 R, 61 P

[56] References Cited

U.S. PATENT DOCUMENTS 3,376,503  4/1968  Lundstrom ...................... 324/61 R
3,448,381  6/1969  Perry ................................ 324/61 R Primary Examiner—Stanley T. Krawczewicz
Attorney, Agent, or Firm—Birch, Stewart, Kolasch & Birch

[57] ABSTRACT

An apparatus for capacitance or dampness measurement is provided. The apparatus is particularly suitable for continuous determination of dampness over substantially flat surfaces such as roofs, floors, pavements and walls. The apparatus essentially includes a pair of substantially elongate electrodes attached to a casing which has a pair of removable surface engaging wheels a handle for pushing and steering, a pair of grip handles for carrying and maneuvering, and two recesses, one for a power supply and the other for an electronic monitoring apparatus combined with a read-out display means. The electrodes are separated by a gap of approximately 5 cm and are retained on the casing so as not to be taut but to be slightly floppy so as to permit good contact between the electrodes and the surface to be tested. The value of capacitance/unit area of the electrodes in air is preferably in the range 50 pFm$^{-2}$–150 pFm$^{-2}$. In use, following the calibration, the apparatus is propelled systematically over the surface to be tested as a manually propelled vehicle. Capacitance readings are taken by observation of the dials of the electronic monitoring apparatus through the opening. When used on walls, the wheels are removed to provide improved contact between the electodes and the wall. In another embodiment, the electrodes also function as tracks, (which are electrically insulated from each other and the casing) for a tracked vehicle. A roller pair for each track, which is endless, is provided.

19 Claims, 8 Drawing Figures

APPARATUS FOR CAPACITANCE OR DAMPNESS MEASUREMENTS

BACKGROUND OF THE INVENTION

1. Field of the Invention

This invention relates to the measurement of electrical capacitance, as applied to the detection and measurement of dampness in structures. It relates in particular to the provision of an apparatus suitable for continuous determination of dampness over substantially flat surfaces such as roofs, floors, pavements and walls.

2. Description of Background Art

It is known to apply a pair of hand held probe type electrodes repeatedly to different locations over a surface to be tested, taking a reading of the capacitance or dampness at each application. Furthermore, existing moisture detectors depend upon changes in dielectric constant of the material in the fringe electrostatic field of coplanar electrodes. Such instruments have limited penetration depth because the fringe (or spray) electrostatic field falls off rapidly as the distance from the electrodes increases. Such instruments find useful applications in, for example, the paper manufacturing industry where the thickness of the paper is small However, for surfaces such as roofs where a penetration depth of several centimetres is required, fringe electrostatic field capacitance instruments do not perform satisfactorily. It is an object of the present invention to provide an apparatus which overcomes these problems.

SUMMARY AND OBJECTIONS OF THE INVENTION

The invention therefore provides an apparatus for capacitance or dampness measurements in a substance having an exposed substantially flat surface, which apparatus comprises a pair of substantially elongate electrodes electrically isolated from each other; means for making a separate electrical connection from each electrode to an electrode monitoring apparatus; and means for moving at least one of the electrodes on or over the surface to permit discrete or continuous measurements of capacitance or dampness to be taken.

In the case where only one of the electrodes is capable of being moved on or over the surface, that electrode is hereinafter referred to as the mobile electrode. If both electrodes are capable of being moved, they are hereinafter referred to as the mobile electrode pair.

When the mobile electrode is in use, the other electrode of the pair is embedded in or located beneath the surface. The mobile electrode or the mobile electrode pair preferably comprises a polymeric material such as carbon black impregnated rubber. Alternatively, the mobile electrode or mobile electrode pair may comprise aluminium foil the exposed or surface oriented face or faces of which have a protective covering of a polymeric material which may be bonded to the foil. Preferably, the means for moving the mobile electrode or the mobile electrode pair comprises a tracked vehicle having an endless track or tracks which also function as the electrode or electrodes as the case may be. In the case of a mobile electrode pair, the tracks run for preference on separate pairs of rollers mounted on the vehicle and are capable of independently rotating to facilitate steering of the vehicle.

The means for making a separate electrical connection between each track and a respective isolated terminal on the body of the vehicle may be of the wire bristle type or the carbon type.

Alternatively, the means for moving the mobile electrode or the mobile electrode pair may comprise a vehicle on which is mounted the mobile electrode or mobile electrode pair which comprise one or two strips respectively. The strip(s), in use, is dragged by the vehicle across the surface to be tested. Such a vehicle is particularily useful for measuring capacitance or dampness in walls.

If desired, the vehicle may additionally comprise a pair of coaxial surface engaging wheels which assist in the movement of the vehicle.

Where a mobile electrode is used, the measurement of the degree of moisture in the substance is obtained by conductivity and clearly no fringe electrostatic field is present other than the usual edge effects of a parallel plate capacitor as the electrodes are not in substantially the same plane but in substantially parallel planes. It has been found that the moisture in the substance under test provides sufficient conductivity which results in the effective distance between the mobile electrode and the electrode in the substance to be reduced. Thus, the greater the percentage of moisture in the substance, the greater the conductivity between the plates.

In the case of coplanar electrodes, it has been found that if the electrode separation distance is in the range 0.5–20 cm the fringe electrostatic field is reduced and the measurement of the degree of moisture in the substance is related to the level of conductivity between the plates via the substance being tested. The electrode separation distance is preferably 5 cm.

The value of the fringe capacitance/unit area between the electrodes at which a mobile electrode pair becomes suitable for the practical detection of moisture in a substance has been found by experiments to be in the region of 100 $pFm^{-2}$ of the total electrode area when measured in air. Higher capacitances are moving into the realm of fringe electrostatic field methods whereas lower capacitances are desirable but very small values may be difficult to achieve within practical dimensional constraints. It is noted, for example, that fringe electrostatic field instruments tend to have small, closly spaced electrodes, typically two plates 5 cm×7 cm each separated by a 0.1 cm gap. It has been found that the fringe capacitance per unit area of these instruments is in the region of 250 $pFm^{-2}$. On the other hand, in the present invention, the fringe electrostatic field capacitance of a mobile electrode pair 30 cm×20 cm each separated by a gap of approximately 5 cm is approximately 65 $pFm^{-2}$. It has been found that by reducing the fringe electrostatic field capacitance to a minimum by increasing the distance between the electrodes and making the electrodes relatively large in area, more accurate detection of moisture in the substance is possible.

The vehicle is preferably adapted to carry the electronic monitoring apparatus. A handle is preferably provided for propelling and steering the vehicle.

BRIEF DESCRIPTION OF THE DRAWINGS

The invention will be understood in greater detail from the following description of a first embodiment and second embodiment thereof, given by way of example only, with reference to the accompanying drawings, in which.

DETAILED DESCRIPTION OF THE INVENTION

Figure 1:
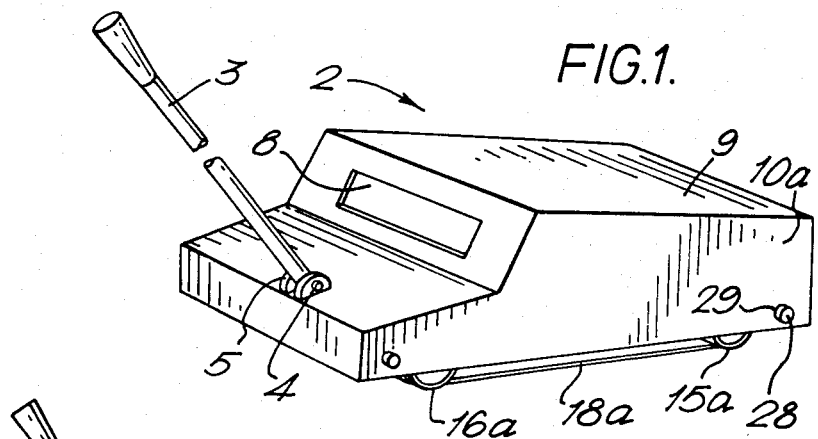
FIG. 1 is a perspective view of a first apparatus.
Figure 2:
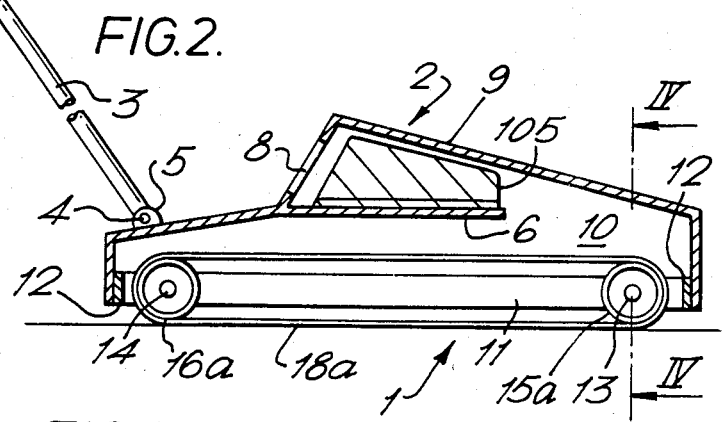
FIG. 2 is a cut-away side elevation of the apparatus of FIG. 1, with the proximate side removed.
Figure 4:
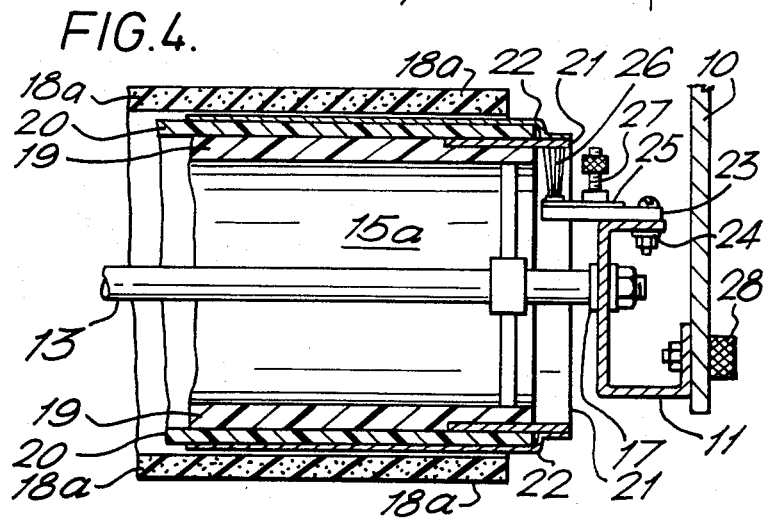
FIG. 4 is a section through the outer end of a roller of the apparatus of FIG. 2, taken along the line IV—IV and viewed in the direction of the associated arrows.
Figure 3:
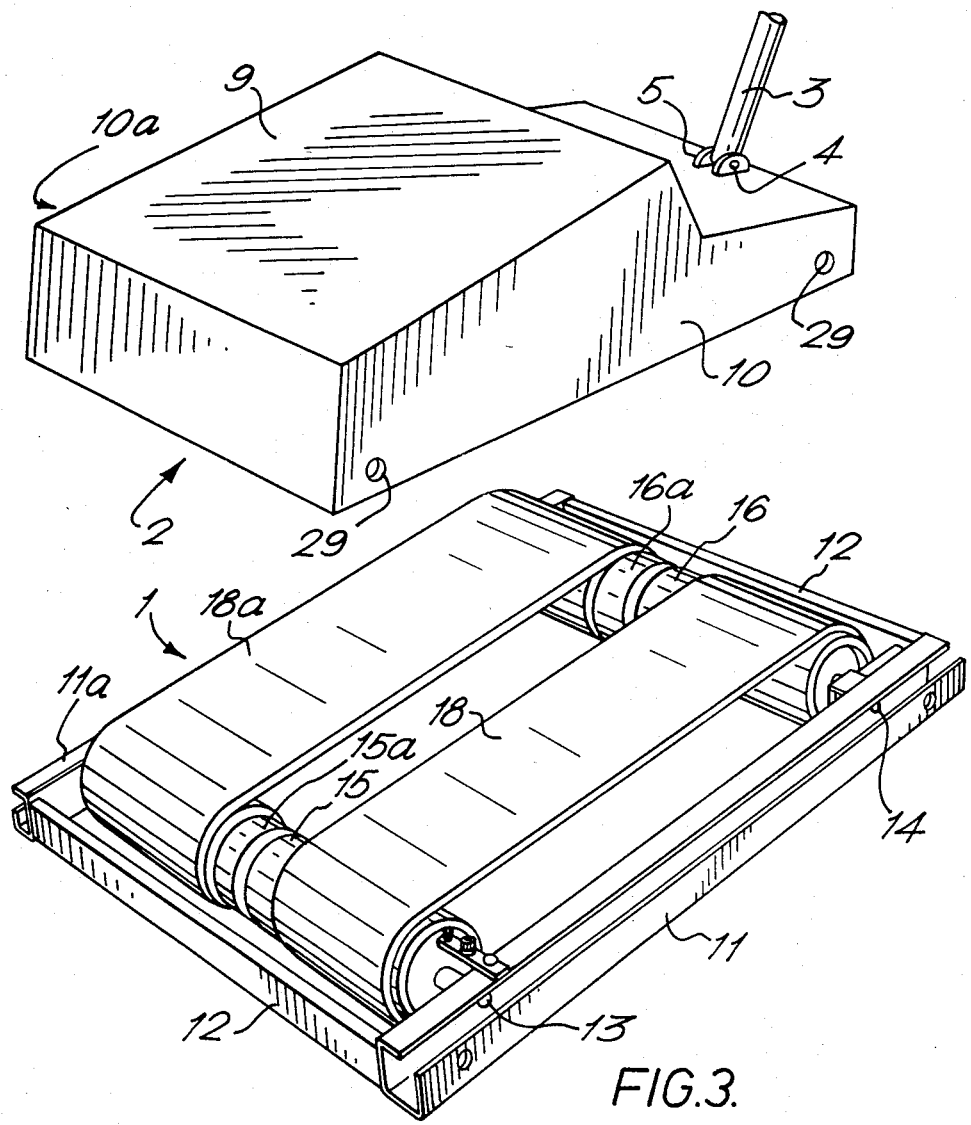
FIG. 3 is an exploded perspective view of the apparatus of FIG. 1, with the cover removed from the chassis.

Referring now to FIGS. 1 to 4 of the drawings, a first apparatus comprises a chassis 1 and a hollow cover 2 having a handle 3 pivotally attached thereto by a horizontal pivot pin 4 held in a pair of lugs 5. The cover 2 comprises a shelf 6 adapted to support an electronic monitoring apparatus 105, an opening 8 through which the dial or dials of the electronic monitoring apparatus 105 can be read, a roof 9 and two side walls 10, 10a.

The cover 2 is detachably attachable to the chassis 1 by means of conventional fasteners 28 (FIG. 4) and corresponding holes 29 in the cover 2.

The chassis comprises side members 11, 11a, transverse members 12, and a pair of axles 13, 14 journalled in the side members 11, 11a by means of journal bearings 17. The axle 13 bears two independently rotatable plastics rollers 16, 16a. The rollers 15, 15a are insulated one from the other and from the chassis 1. The rollers 16, 16a are similarily insulated. The roller pair 15, 16 carries an endless track 18 of polymeric material such as carbon black impregnated rubber, an electrically conducting material. The roller pair 15a, 16a carries a similar track 18a. The tracks 18 and 18a function as a mobile electrode pair and are separated by a gap of approximately 5 cm. It will be appreciated therefore that the tracks 18, 18a are insulated from each other and from the chassis 1.

The roller 15a (FIG. 4) comprises a plastics core 19, a plastics sleeve 20 and a projecting cuff 21 which is located in a terminal rebate of the core 19 and securely held between the core 19 and the sleeve 20. The cuff 21 is of electrically conducting metal. A layer 22 of electrically conducting composition coats the outside of the sleeve 20 and the outside of the projecting part of the cuff 21 to establish a satisfactory electrical connection between the track 18a and the cuff 21.

The side member 11 carries a brush platform 23 of insulating material fixed thereto by conventional fastening means 24. The brush platform carries a conducting plate 25 which in turn carries an electrical brush 26 and a screw connector 27. The brush 26 is arranged to make continuous electrical contact with the inner aspect of the projecting part of the cuff 21 during rotation of the roller 15a. The screw connector 27 enables a standard wire connection to be made with the electronic monitoring apparatus 105, which latter is accordingly in continuous electrical communication with the track 18a.

The roller 15 is constructed similarily to the roller 15a, and a similar electrical brush and screw connector are provided for the roller 15 as those described above in connection with the roller 15a.

The rollers 16, 16a on the other hand, comprise respective cores and sleeves similar to core 19 and sleeve 20, but do not have any conducting cuffs nor layer of electrically conducting composition, nor are they provided with any electrical brushes or screw connectors. The function of rollers 16, 16a is purely the mechanical support of electrical insulation of the tracks 18 and 18a respectively.

In use, the first apparatus is placed upon a flat surface such as a roof, in respect of which it is desired to locate damp areas and/or estimate the degree of saturation by moisture. The first apparatus is propelled systematically over the structural surface as a manually propelled vehicle using the handle 3; meanwhile capacitance readings are taken by observation of the dial(s) of the electronic monitoring apparatus 105 through the opening 8. Thus for example a rectangular grid can be drawn or projected onto the structural surface and the numbered cells thereof covered in systematic successions by the first apparatus a capacitance reading being taken and recorded in respect of each numbered cell.

When the survey of the surface has been completed, core samples should be taken from the surface at least from four locations namely:

1. Location giving minimum reading;
2. Location giving maximum reading;
3. Location giving $\frac{1}{3}$ of maximum reading; and
4. Location giving $\frac{2}{3}$ of maximum reading.

The samples are then examined visually for moisture content and/or may be dried in an oven so as to evaporate moisture there in to provide quantitative analysis of moisture content.

Alternatively, a probe type meter may be inserted into the selected locations to give an indication of the moisture content of the surface. From these four readings a profile of the moisture content of the surface may be determined.

It will be understood that the electronic monitoring apparatus 105 may incorporate automatic recording equipment for capacitance measurements, and manually operated recording equipment for correlating each said measurement with a reference for identifying the relevant region of the structural surface.

It should be observed that the use of the layers 22 of electrically conducting composition in the rollers 15, 15a is regarded at present as a laboratory expedient only, and a simpler arrangement will probably replace it in the near future, for establishing electrical contact between the tracks of the vehicle and respective insulated terminals on the body thereof.

Figure 5:
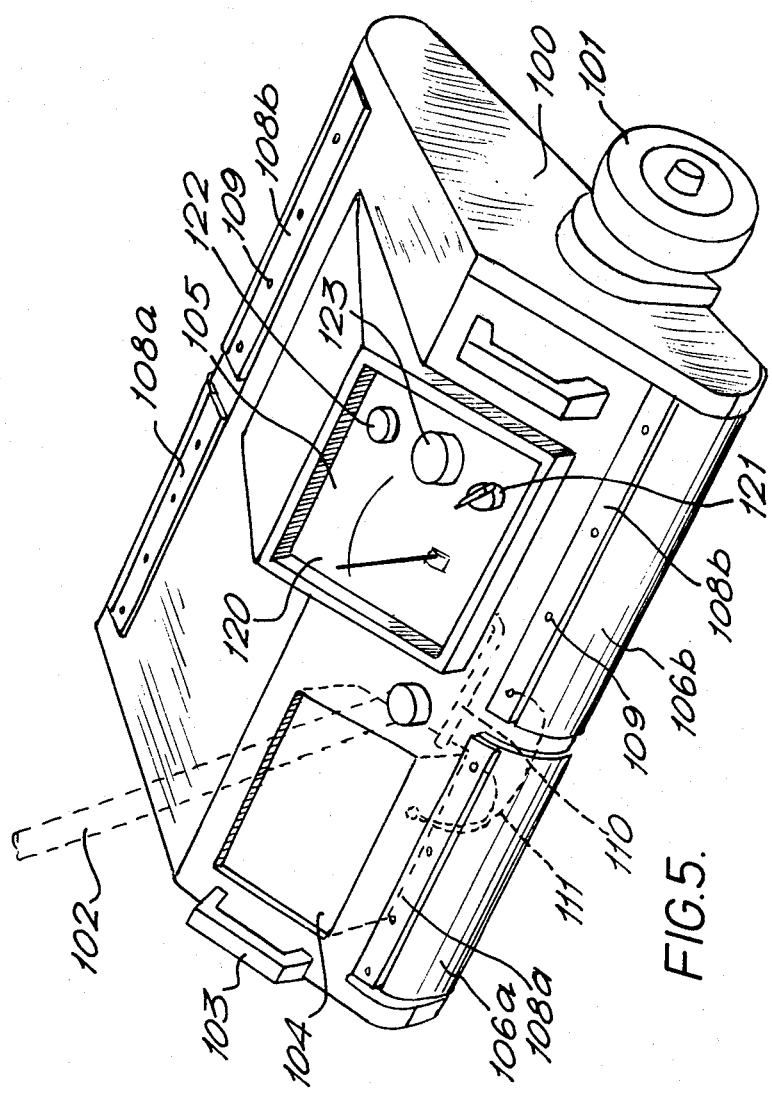
FIG. 5 is a perspective view of a second apparatus.
Figure 6:
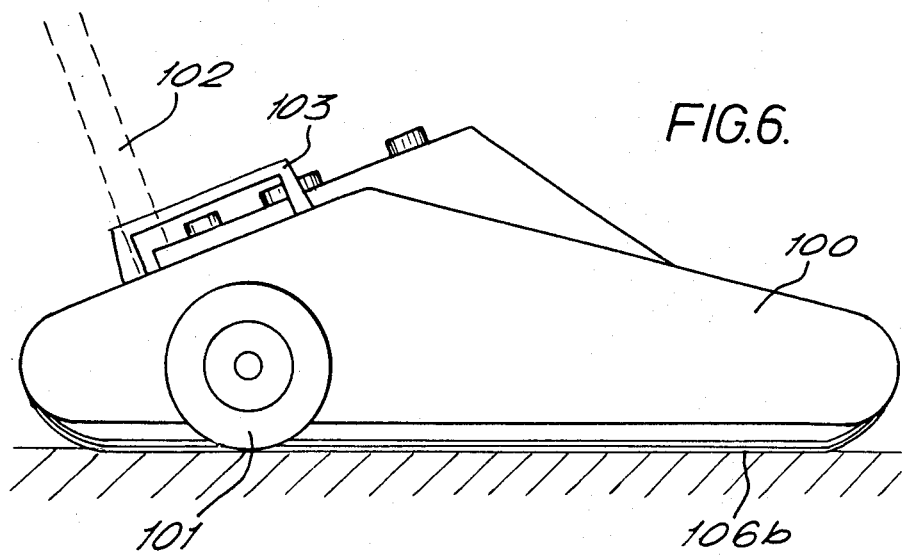
FIG. 6 is a side elevation of the apparatus of FIG. 5.
Figure 7:
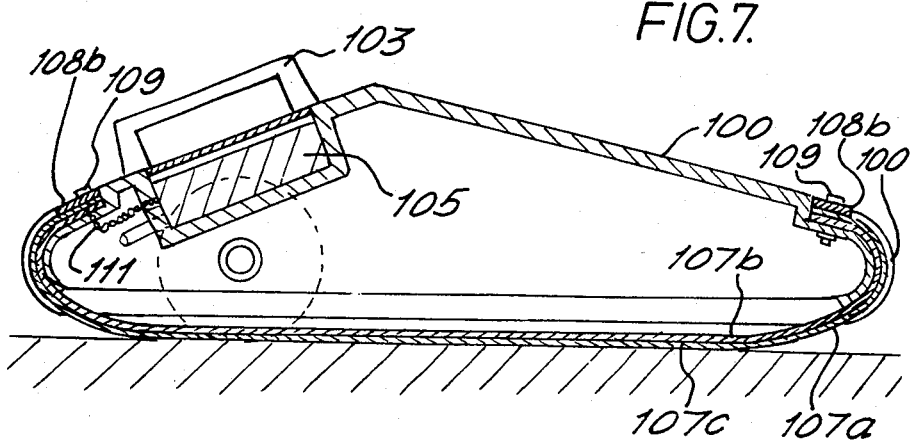
FIG. 7 is a cut-away side elevation of the apparatus of FIG. 5 with the proximate casing removed and FIG. 8 is a schematic view of an electronic monitoring apparatus for use in the apparatus of FIGS. 1–7.

Referring now to FIGS. 5 to 7 of the drawings, a second apparatus comprises a casing 100 having a pair of removable surface engaging wheels 101, a handle 102 for pushing and steering, a pair of grip handles 103 for carrying and manoeuvering, and two recesses, one for a power supply 104 and the other for an electronic monitoring apparatus 105 combined with a read-out display means 120. The read-out display means 120 is located in the casing so as to be visible to the operator when in use. The casing 100 carries a pair of carbon black impregnated rubber strips 106a and 106b which function as a mobile electrode pair. Each of the strips 106a and 106b each comprises a layer of rubber (107a and 107b FIG. 7) having a thin aluminium foil 107c sandwiched therebetween. The strips 106a and 106b are retained on the casing by a respective pair of battens 108a and conventional nuts and bolts 109. The strips 106a and 106b are electrically insulated from each other and from the casing 100 and separated by a gap of about 5 cm. The strips 106a and 106b are retained on the casing 100 so as not to be taut under the body of the casing 100 but to be slightly floppy to permit good contact between the strips 106a and 106b and a surface to be traversed. The power supply 104 is connected to the electronic monitoring apparatus 105 via cables 110 while each strip 106a and 106b is also connected to the electronic monitoring apparatus 105 via cables 111 which for convenience are routed through the power supply recess 104.

Figure 8:
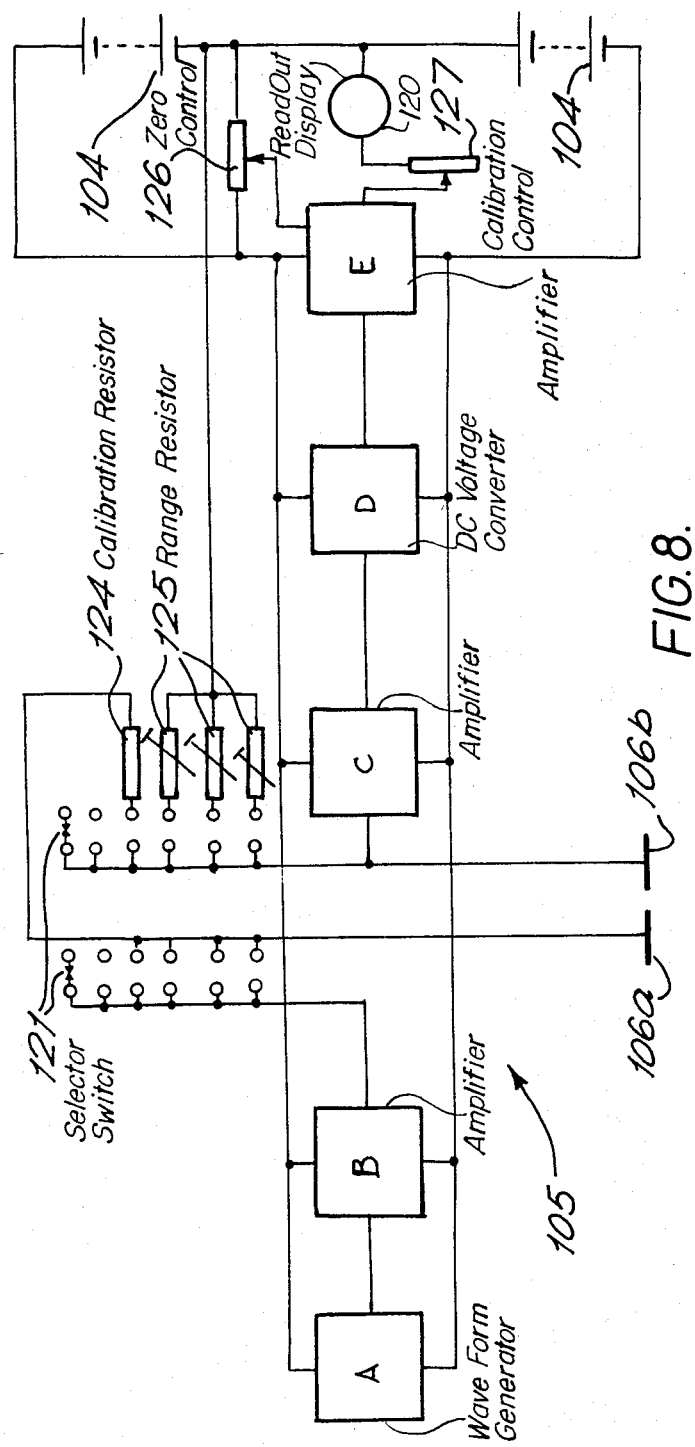

Referring now to FIGS. 5 and 8 of the drawings, the electronic monitoring apparatus 105 comprises a wave form generator A, amplifiers B, C and E, and a DC voltage converter D. The apparatus further comprises an on/off, function selector and range selector switch 121, a calibration knob 122 a zero control knob 123, a read-out display means 120 (which is an analogue voltmeter), a calibration resistor 124, range resistors 125, a zero control 126 and a calibration control 127.

The apparatus 105 which may be used on either of the embodiments described herein operates as follows:

The wave form generator A feeds the amplifier B with wave form. The wave form is fed to the strip 106a via the function selector switch 121. The wave form is coupled, by means of electrical capacitance, to the strip 106b. The wave form from the strip 106b is fed to the range resistor 125 and also to the amplifier C the output of which is fed to the DC voltage converter D. The output from the DC voltage converter D is fed to the amplifier E the output of which is fed via the display calibration control 127 to the read-out display means 120 (analogue voltmeter). Thus, the DC voltage which is measured across the output of amplifier E is in direct relationship with the value of the capacitance between the strips 106a and 106b. The capacitance of the strips 106a and 106b alters in direct relationship with the amount of moisture in or below the surface to be tested. Thus, the DC voltage which is measured across the output of amplifier E is in direct relationship with the amount of moisture in or below the surface to be tested. The range resistors 125 provide three ranges of sensitivity for the apparatus. The calibration of the electronic monitoring apparatus 105 is carried out prior to each test with the first (or second) apparatus by turning the function selector switch 121 to "calibrate" which brings into the circuit the calibration resistor 124. The zero control knob 123 is turned to "max" which means that the zero control provides no zero offset. The calibration control 127 is then adjusted to read full scale on the read-out display means 120.

The second apparatus referred to above is used in a manner similar to that described with respect to the first apparatus.

However, in the first embodiment described with respect to FIGS. 1-4 of the drawings, the electrodes also function as tracks on which the vehicle rides. In the present embodiment, the electrodes are dragged beneath the vehicle, movement being assisted by the wheels 101 thereon. If it is desired to detect moisture in walls, it has been found to be more convenient to remove the wheels 101 and to push the vehicle against the wall so as to drag the electrodes across the surface thereof.

For practical roof moisture detection, a coplanar electrode arrangement like those just described is usually preferable. However, in situations where it is required to detect moisture at depths in excess of approximately 5 cm, the pair of electrodes comprise one electrode (the mobile electrode) which is moved across the surface to be surveyed in a manner similar to that described with respect to the previous examples, the second electrode of the pair comprising, in the case of a roof having a metal deck, the deck itself or, if a metal deck is not present, by insertion of a metal probe at a point as low as possible in the surface material to be tested. Such a situation may be present in cold climate roofs where very thick insulation is used and it is desired to detect moisture as low as possible in the surface to be tested.

From the metal deck or probe, a suitable connection is made to the electronic monitoring apparatus by means of a long connecting wire. By incorporating additional switches on the apparatus of the preferred embodiments previously described, the electrical connection from one of the electrodes of the mobile electrode pair is disconnected from the electronic monitoring apparatus, a connection instead being made to the metal deck or probe as the case may be. The modified apparatus may be used in a manner similar to that described with respect to the first or second apparatus previously described.

It will be appreciated that what has been described particularily refers to roofs. However, the apparatus can easily be used on walls, sloping surfaces or pavements.

1. An apparatus for capacitance or dampness measurement in a substance having an exposed substantially flat surface which apparatus comprises:
   a pair of substantially elongate co-planar electrodes electrically isolated from each other and defining a gap therebetween of at least 0.5 cm;
   means for making a separate electrical connection from each said electrode to an electrode monitoring apparatus;
   means for moving the electrodes on the surface to permit discreet or continuous measurements of capacitance or dampness to be taken;
   wherein each said electrode comprises an electrically conductive polymeric material;
   said means for moving each said electrode comprises a tracked vehicle having a pair of endless tracks thereon; and
   each of said tracks functions as one of said electrodes.

2. An apparatus as claimed in claim 1 wherein each of said tracks runs on a separate pair of rollers mounted on the vehicle and each of said tracks is capable of independently rotating to facilitate steering of the vehicle.

3. An apparatus as claimed in claim 2 wherein the means for making a separate electrical connection between each said track and a respective isolated terminal on the body of the vehicle comprises an electrical brush of a wire bristle or carbon type.

4. An apparatus as claimed in claim 3 wherein the electrodes are separated by a gap of between 0.5 cm and 20 cm.

5. An apparatus as claimed in claim 4 wherein the gap is approximately 5 cm.

6. An apparatus as claimed in claim 5 wherein the value of capacitance/unit area of the electrode in air is in the range 50 $pFM^{-2}$–150 $pFM^{-2}$.

7. An apparatus as claimed in claim 6 wherein the surface is a roof.

8. An apparatus for capacitance or dampness measurement in a substance having an exposed substantially flat surface which apparatus comprises:

a pair of substantially elongate co-planar electrodes electrically isolated from each other and defining a gap therebetween of at least 0.5 cm;

means for making a separate electrical connection from each electrode to an electrode monitoring apparatus;

means for moving the electrodes on the surface to permit discreet or continuous measurements of capacitance or dampness to be taken;

wherein each said electrode comprises aluminum foil;

polymeric material being positioned as a protective medium between the surface and each electrode;

said means for moving each electrode includes a vehicle; and each said electrode is in the form of a strip which in use is protected by said polymeric material while being dragged beneath the vehicle across the surface to be tested.

9. An apparatus as claimed in claim 8 wherein the vehicle additionally comprises a pair of coaxial surface engaging wheels thereon which assist in the movement of the vehicle.

10. An apparatus as claimed in claim 9 wherein each electrode is separated by a gap of between 0.5 cm and 20 cm.

11. An apparatus as claimed in claim 10 wherein the gap is approximately 5 cm.

12. An apparatus as claimed in claim 11 wherein the value of capacitance/unit area of the electrode in air is in the range 50 $pFm^{-2}$–150 $pFm^{-2}$.

13. An apparatus as claimed in claim 12 wherein the surface is a roof.

14. An apparatus for capacitance or dampness measurement in a substance having an exposed substantially flat surface which apparatus comprises:

a pair of substantially elongate co-planar electrodes electrically isolated from each other and defining a gap therebetween of at least 0.5 cm;

means for making a separate electrical connection from each electrode to an electrode monitoring apparatus;

means for moving the electrodes on the surface to permit discreet or continuous measurements of capacitance or dampness to be taken;

wherein each said electrode comprises an electrically conductive polymeric material;

said means for moving each electrode includes a vehicle; and wherein each said electrode is in the form of a strip which in use is dragged beneath the vehicle across the surface to be tested.

15. An apparatus as claimed in claim 14 wherein the vehicle additionally comprises a pair of coaxial surface engaging wheels thereon which assist in the movement of the vehicle.

16. An apparatus as claimed in claim 15 wherein each electrode is separated by a gap of between 0.5 cm and 20 cm.

17. An apparatus as claimed in claim 16 wherein the gap is approximately 5 cm.

18. An apparatus as claimed in claim 17 wherein the value of capacitance/unit area of the electrode in air is in the range 50 $pFm^{-2}$–150 $pFm^{-2}$.

19. An apparatus as claimed in claim 18 wherein the surface is a roof.

* * * * *